(12) United States Patent
Bordewick et al.

(10) Patent No.: US 6,418,928 B1
(45) Date of Patent: Jul. 16, 2002

(54) MULTI-SEAL RESPIRATOR MASK

(75) Inventors: Steven S. Bordewick, Shoreview; Gary Hansen, Eden Prairie, both of MN (US)

(73) Assignee: Mallinckrodt Inc., St. Louis, MO (US)

( * ) Notice: Subject to any disclaimer, the term of this patent is extended or adjusted under 35 U.S.C. 154(b) by 0 days.

(21) Appl. No.: 09/668,176

(22) Filed: Sep. 25, 2000

(51) Int. Cl.⁷ .................................. A62B 18/02
(52) U.S. Cl. ..................... 128/205.25; 128/206.26; 128/207.13; 128/207.18
(58) Field of Search ................ 128/200.24, 201.12, 128/201.19, 201.24, 205.25, 206.12, 206.14, 206.15, 206.18, 206.19, 206.21, 206.23, 206.24, 206.26, 206.28, 207.11, 207.13, 207.18

(56) References Cited

U.S. PATENT DOCUMENTS

| | | |
|---|---|---|
| 2,939,458 A | 6/1960 | Lundquist |
| 3,545,436 A | 12/1970 | Holloway |
| 4,167,185 A | 9/1979 | Lewis |
| 4,248,218 A * | 2/1981 | Fischer .................. 128/204.18 |
| 4,263,908 A | 4/1981 | Mizerak |
| D262,322 S | 12/1981 | Mizerak |
| 4,677,977 A | 7/1987 | Wilcox |
| 4,739,755 A | 4/1988 | White et al. |
| 4,782,832 A | 11/1988 | Trimble et al. |
| 4,907,584 A | 3/1990 | McGinnis |
| 4,944,310 A | 7/1990 | Sullivan |
| 4,971,051 A | 11/1990 | Toffolon |
| 5,005,571 A | 4/1991 | Dietz |
| 5,243,971 A | 9/1993 | Sullivan et al. |
| 5,265,595 A | 11/1993 | Rudolph |
| 5,355,878 A | 10/1994 | Griffiths et al. |
| 5,540,223 A | 7/1996 | Starr et al. |
| RE35,339 E | 10/1996 | Rapoport |
| 5,560,354 A | 10/1996 | Berthon-Jones et al. |
| 5,655,527 A | 8/1997 | Scarberry et al. |
| 5,724,965 A * | 3/1998 | Handke et al. ......... 128/207.13 |

FOREIGN PATENT DOCUMENTS

EP    462701    12/1991

OTHER PUBLICATIONS

W. Cleghorn, PhD, "Respiration Team," Ontario Rehabilitation Technology Consortium Website, Apr. 20, 2000, pp. 1–2.

* cited by examiner

Primary Examiner—Glenn K. Dawson
(74) Attorney, Agent, or Firm—Rothwell, Figg, Ernst & Manbeck

(57) ABSTRACT

A respirator mask includes an inner plenum with a gas inlet and a manifold adapted to fit under the nose of a wearer, a pair of nasal inserts projecting from the manifold to define primary seals with the nasal passages of the wearer, an outer plenum adapted to surround at least the nose of the wearer, a secondary seal mounted on an outer edge of the outer plenum and adapted to contact the face of the wearer around the nose in air tight relation, and at least one opening formed in the inner plenum to permit gas to flow into the outer plenum. By pressurizing the outer plenum, the mask decreases the pressure differential between the interior of the mask and the outside atmosphere to reduce the gas flow rate out of the mask in the event of a leak. Diversion of gas into the outer plenum also allows use of an inflatable secondary seal to maintain air-tight contact with the face of the user.

14 Claims, 2 Drawing Sheets

MULTI-SEAL RESPIRATOR MASK

BACKGROUND OF THE INVENTION

1. Field of the Invention

The present invention relates generally to the field of respirator masks.

2. Description of the Background Art

A respirator mask is a device used to deliver a gas or gases to a patient. In its simplest form, the respirator mask includes a face piece, headgear for attaching the face piece to the head of the patient, and a gas supply hose. The respirator mask can be used to deliver a variety of gases, including air or oxygen, and a variety of medicines or treatments.

In recent years, respirator masks have been used in the treatment of obstructive sleep apnea and other respiratory illnesses. Treatment of obstructive sleep apnea using a respirator mask is known as continuous positive airway pressure (CPAP) therapy. The therapy is typically administered at night while the patient is asleep and involves placing a respirator mask over the nose and mouth of the patient during sleep. Positive air pressure from an air compressor or blower is forced through the respirator mask into the patient's airway via the nasal passages to keep the airway open.

An impediment to effective CPAP therapy is the occurrence of air leakage between the skin and the mask seal. Even very small leaks can be perceived by the wearer, who then compensates by increasing the pressure of the mask against the face. While reducing leakage, this action may cause skin irritation and injury. In either case, sleep is interrupted, putting the effectiveness of the therapy at risk.

A variety of mask seals have been developed to improve patient comfort by reducing leakage from the mask. One type of respirator mask, exemplified by U.S. Pat. Nos. 4,907,584, 4,971,051, and 5,540,223, relies on direct compression of an elastomeric cushion against the skin to form a primary seal. Another type of respirator mask, exemplified by U.S. Pat. Nos. 5,243,971, 5,655,527, and 4,167,185, relies on a "reverse flap" that is held against the skin by the internal air pressure of the mask. In both types of mask, a single seal of varying area stands between the high-pressure air inside the mask and the outside atmosphere. Inevitably, the fit of such masks is not perfect, and the patient must compensate for any fitting inaccuracy by tightening the headgear that is used to attach the mask to the head of the wearer. The result is either leakage or painful pressure points against the skin.

Yet another type of respirator mask, exemplified by U.S. Pat. No. 4,739,755, utilizes a seal with multiple edges to enhance sealing efficiency. In this type of mask, both seal edges are approximately conterminous, extending about the nose with approximately the same perimeter. Thus, inaccuracies in fit are likely to affect both edges.

There remains a need in the art for an improved respirator mask.

SUMMARY OF THE INVENTION

A respirator mask is provided according to a first aspect of the present invention. The respirator mask includes an inner plenum with a gas inlet and a manifold adapted to fit under the nose of a patient, a pair of nasal inserts projecting from apertures in the manifold to define primary seals with the nasal passages of the patient, an outer plenum adapted to surround at least the nose of the patient, a secondary seal mounted on an outer edge of the outer plenum and adapted to contact the face of the patient around the nose in air tight relation, and at least one opening formed in the inner plenum to permit gas to flow from the inner plenum into the outer plenum. By pressurizing the outer plenum, the mask of the present invention decreases the pressure differential between the interior of the mask and the outside atmosphere to reduce the gas flow rate out of the mask in the event of a leak. Diversion of gas into the outer plenum also allows use of an inflatable secondary seal to maintain air-tight contact with the face of the user.

A method of treating a respiratory ailment is provided according to a second aspect of the present invention. The method includes connecting a source of pressurized gas to an inner plenum of a respirator mask having an outer plenum configured to cover only the nose of a patient, mounting the respirator mask to the face of a patient over the patient's nose such that nasal inserts carried by the inner plenum form substantially air-tight primary seals with the patient's nasal passages and the outer plenum forms a substantially air-tight secondary seal around the patient's nose, and activating the source of pressurized gas to supply positive gas pressure to the mask, wherein a portion of the pressurized gas is permitted to flow from the inner plenum to the outer plenum via an opening to create a region of intermediate pressure between the primary and secondary seals.

The above and other features and advantages of the present invention will be further understood from the following description of the preferred embodiments thereof, taken in conjunction with the accompanying drawings wherein like elements are referred to using the same reference numerals.

DETAILED DESCRIPTION OF THE PREFERRED EMBODIMENT

Figure 1:
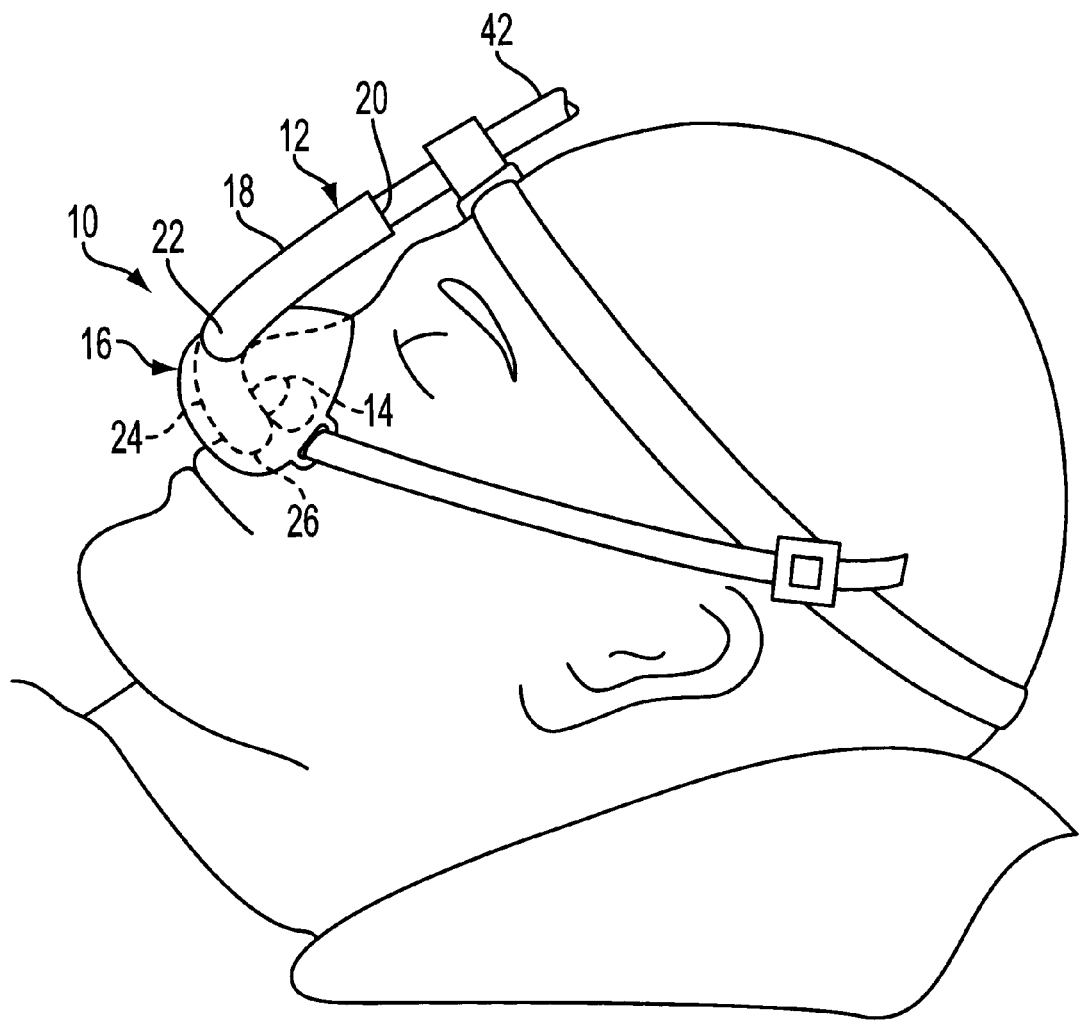
FIG. 1 shows a side view of a respirator mask of the present invention secured to the head of a patient.

FIG. 1 shows a respirator mask 10 of the present invention secured to the head of a patient. Respirator mask 10 includes an inner plenum 12 adapted to convey a gas to a pair of nasal inserts 14 forming primary seals with the patient's nasal passages and an outer plenum 16 extending from the inner plenum to a secondary seal surrounding the patient's nose. One or more holes are formed in a portion of the inner plenum within the outer plenum so that some of the gas flowing through the inner plenum is diverted into the outer plenum via the holes to pressurize the outer plenum thereby decreasing the pressure differential between the interior of the mask and the outside atmosphere to reduce the gas flow rate out of the mask in the event of a leak. Diversion of gas into the outer plenum also allows optional use of an inflatable secondary seal to improve contact with the face of the user.

Figure 2:
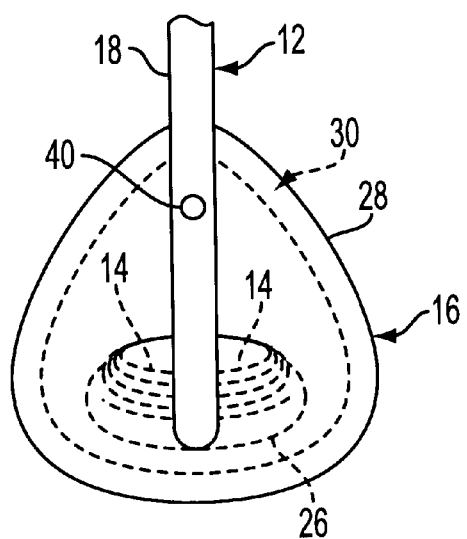
FIG. 2 shows an enlarged frontal view of the respirator mask illustrating further detail.
Figure 3:
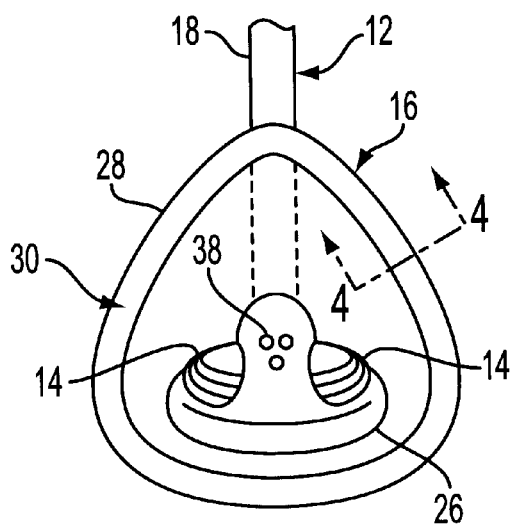
FIG. 3 shows an enlarged rear view of the respirator mask illustrating further detail.

Inner plenum 12 is shown as a tubular member having a first portion 18 extending from a gas inlet 20 to a bend 22, and a second portion 24 extending from the bend at an angle relative to the first portion. Preferably, the angle is chosen such that, when mask 10 is secured to a patient's head as shown in FIG. 1, the first portion of inner plenum 12 extends longitudinally along the bridge of the patient's nose and the second portion bends inwardly toward the patient. It will be appreciated, however, that the inner plenum can be configured to approach the face of a patient from any direction including, by way of example, configurations where the inner plenum extends laterally from one or both sides of the patient's face, where the inner plenum extends upwardly from beneath the outer plenum, or where the inner plenum extends approximately perpendicular to the patient's face. As best seen in FIGS. 2 and 3, the second portion of inner plenum 12 spreads laterally outward in the direction of the patient to define a manifold 26 spanning both nostrils of the patient. The inner plenum is preferably formed of a rigid or semi-rigid material of a type normally used to form a plenum in a respirator mask. Silicones, urethanes, and polyvinyl chloride (PVC) are examples of suitable materials.

Nasal inserts 14 are mounted over apertures (not shown) formed in the manifold in laterally spaced relation to deliver gas to the patient's nostrils. In the embodiment illustrated in FIGS. 2 and 3, the nasal inserts are similar to those described in U.S. Pat. No. 4,782,832 to Trimble et al., the disclosure of which is incorporated herein by reference. The inserts shown in FIGS. 2 and 3 are generally frustoconical and mounted on a bellows-type corrugated section, with a central air passageway formed therethrough to permit gas flow into the nose. The inserts are preferably formed of a soft synthetic resin material, such as silicone, so as to allow axial and radial adjustment of the inserts to accommodate variations in the nasal passages of different wearers. While a particular type of nasal insert is shown and described, it will be appreciated that any type of nasal insert capable of forming a seal with a nasal passage can be used.

Referring still to FIGS. 2 and 3, outer plenum 16 is shown as a convex shell with a peripheral edge 28 adapted to mount secondary seal 30. The shell is preferably formed of a rigid or semi-rigid material of a type normally used to form a respirator mask shell (e.g., silicones, urethanes, or PVC) and is generally triangular in configuration with rounded corners to fit around the nose of a patient. The first portion of inner plenum 12 extends along an exterior of outer plenum 16 and bends inwardly such that the second inner plenum portion 24 is disposed within the outer plenum as shown in FIG. 1.

Figure 4:
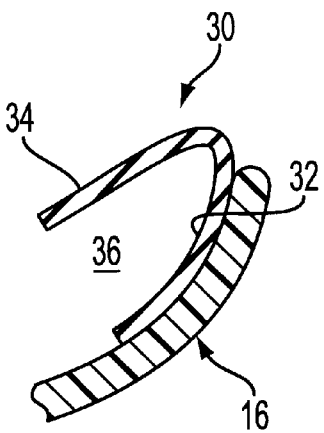
FIG. 4 shows a fragmentary cross-sectional view of the respirator mask taken through line 4—4 in FIG. 3.

Secondary seal 30 is shown as a highly flexible strip of elastomeric material secured to the outer peripheral edge of the shell. Referring to FIG. 4, it can be seen that the strip is generally U-shaped in cross-section, with one side 32 being affixed to the shell adjacent the outer peripheral edge and the other side 34 bending inwardly therefrom to define a space 36 between the opposite sides of the seal. The seal is preformed to generally follow the contours of the patient's face and will inflate to maintain air-tight contact therewith when the pressure within space 36 defined by the seal is greater than the pressure outside the mask. The seal described above is similar to that disclosed in U.S. Pat. No. 4,167,185 to Lewis, the disclosure of which is incorporated herein by reference. It will be appreciated, however, that any suitable seal can be used to maintain air-tight contact with the face of the patient. Suitable seals include those which rely on direct compression of an elastomeric cushion as well as those which rely on a reverse flap or other type of flexible member held against the skin by internal pressure.

Referring to FIG. 3, one or more holes 38 are formed in the portion of inner plenum 12 within outer plenum 16 so that gas flowing from the inner plenum via the holes will pressurize the outer plenum. Three circular holes are shown formed upstream of nasal inserts 14 on an upper surface of manifold 26; however, any number of holes of various shape and size can be formed anywhere along the inner plenum so long as they permit gas flow into the outer plenum. If desired, holes can be formed on more than one side of the inner plenum. To improve comfort, the holes can be placed on either side of the inner plenum to direct the flow of gas away from the nose and face. This prevents the gas from jetting directly against the skin of the patient. The holes are preferably configured to divert a portion of the gases flowing through the inner plenum into the outer plenum to establish an intermediate pressure therein which is less than or equal to the gas pressure in the inner plenum but greater than the air pressure outside the mask. The size of the holes is chosen to establish a desired flow rate for a given range of medically useful pressures in the inner plenum (e.g., about 3 to 35 cm $H_2O$). The flow rate determines how quickly the outer seal will "reinflate" after the occurrence of a leak. Too low a flow rate into the outer plenum would leave the outer or secondary seal flaccid, whereas too great a flow rate would allow excessive flow out of the mask in the event of a leak. The size of the holes is preferably chosen to establish a flow rate of about 0.01 to 1.0 liter/second into the outer plenum in response to an inner plenum pressure of roughly 3 to 35 cm $H_2O$; however, other flow rates can be used in determining the size of the holes.

Referring to FIG. 2, a vent aperture 40 is formed on a portion of inner plenum 12 outside outer plenum 16, preferably on a distal side of the inner plenum opposite the patient's face. The vent aperture can have any configuration to expel the carbon-dioxide laden gases exhaled by the patient between breaths including, by way of example, the vent configuration described in the U.S. Pat. No. 5,065,756 to Rapoport, reissued as RE. 35,339, the disclosure of which is incorporated herein by reference.

In the embodiment shown in FIG. 1, mask 10 is secured to the head of a patient with headgear 50 in the form of straps 51 and 52. Strap 52 is configured to extend circumferentially around the top of the patient's head, and straps 51 are configured to extend diagonally from opposite sides of outer plenum 16 to connectors 53 on strap 52. Connectors 53 are configured to permit adjustment of the tension of the straps which are preferably formed of an elastic fabric.

In use, respirator mask 10 is placed over the head of a patient with straps 51 and 52 loosened so that outer plenum 16 can be positioned over the patient's nose. The mask is then adjusted so that nasal inserts 14 slide into the nostrils of the patient to form primary seals with the nasal passages, after which the straps are tightened to hold the mask in place. A gas delivery hose 42 is attached to the inlet end of inner plenum 12 to convey gas at a predetermined pressure from a source such as a blower (not shown) to the patient through the mask. Gas received at inlet 20 flows through the inner plenum toward the nasal inserts; however, a portion of the gas flowing through the inner plenum is diverted through the openings 38 upstream of the nasal inserts. The diverted gas fills outer plenum 16 at an intermediate pressure less than or equal to the gas pressure in the inner plenum but greater than atmospheric pressure outside the mask. As a result, a positive pressure is created in the outer plenum thereby inflating secondary seal 30 so that an air-tight seal is maintained about the periphery of the outer plenum. Under normal circumstances, the intermediate pressure should approximately equal the pressure of the inner plenum. In the event of a leak, the intermediate pressure may drop, and the resulting lower pressure differential between the outer plenum and the outside air will result in a lower leak flow rate. The gas flow rate into the outer plenum should thus exceed the leak flow rate, allowing the secondary seal to quickly reinflate (e.g., within about one second).

The remaining gas flows into the nose of the patient through the air passages in the nasal inserts. During exhalation, gases exhaled from the patient flow through the inner plenum and are expelled through vent 40 in the outer wall of the inner plenum.

The respirator mask of the present invention can be used to deliver one or more gases to a wearer in connection with any type of respiratory therapy, but is particularly useful in administering CPAP therapy to patients suffering from obstructive sleep apnea.

While the respiratory mask is shown secured to the head of a wearer with a particular configuration of straps, it will be appreciated that the mask can be attached to the wearer using any suitable headgear including, by way of example, anchors biased against the wearer's head as described in U.S. patent application Ser. No. 09/276,799, filed on Mar. 26, 1999, the disclosure of which is incorporated herein by reference.

The inner plenum can have any configuration to convey a gas to the nasal inserts including configurations wherein a gas supply tube passes laterally underneath the nostrils from sides of the face to the nasal inserts, and configurations wherein a gas supply tube enters the mask in generally perpendicular relation to the face. While one gas inlet is shown, it will be appreciated that the inner plenum can have more than one gas inlet. Similarly, the inner plenum can have a single manifold fed from one gas inlet, or multiple manifolds fed from one or multiple gas inlets.

The outer plenum can be configured to cover only the nose or both the nose and mouth of a patient. The inner and outer plenums can be formed separately and joined together using conventional techniques such as adhesive bonding, mechanical attachment, co-molding, and laser welding. Alternatively, the plenums can be integrally formed as a one-piece unit.

While the invention has been described in detail above, the invention is not intended to be limited to the specific embodiments as described. It is evident that those skilled in the art may now make numerous uses and modifications of and departures from the specific embodiments described herein without departing from the inventive concepts.

What is claimed is:

1. A respirator mask for delivering a gas to a wearer comprising:
   an inner plenum with a gas inlet and a manifold adapted to fit under the nose of the wearer;
   a pair of nasal inserts projecting from said manifold for insertion into the nostrils of the wearer to deliver the gas, said nasal inserts defining primary seals adapted to contact the nasal passages in air tight relation;
   an outer plenum extending from said inner plenum to an outer edge adapted to surround at least the nose of the wearer;
   a secondary seal mounted on said outer edge of said outer plenum and adapted to contact the face of the wearer around the nose in air tight relation; and
   at least one opening formed in said inner plenum to permit gas to flow into said outer plenum.

2. The respirator mask of claim 1, wherein said at least one opening is configured to establish an intermediate pressure in said outer plenum which is greater than the pressure outside said outer plenum.

3. The respirator mask of claim 1, wherein said outer plenum is adapted to surround only the nose of the wearer.

4. The respirator mask of claim 3, wherein said inner plenum includes a tubular member adapted to extend along the bridge of the wearer's nose and bend inwardly to connect with said manifold.

5. The respirator mask of claim 4, wherein said manifold projects laterally outward in opposite directions from said tubular member.

6. The respirator mask of claim 5, wherein said nasal inserts are laterally spaced on said manifold.

7. The respirator mask of claim 6, wherein said nasal inserts are formed of a soft, compliant material allowing axial and radial adjustment of said inserts to accommodate variations in the nasal passages of different wearers.

8. The respirator mask of claim 1, further comprising headgear for securing the mask to the head of a patient.

9. A respirator mask for delivering a gas to a wearer comprising:
   an inner plenum with a gas inlet and a manifold adapted to fit under the nose of the wearer;
   a pair of nasal inserts projecting from said manifold for insertion into the nostrils of the wearer to deliver the gas, said nasal inserts defining primary seals adapted to contact the nasal passages in air tight relation;
   an outer plenum extending from said inner plenum to an outer edge adapted to surround at least the nose of the wearer;
   a secondary seal mounted on said outer edge of said outer plenum and adapted to contact the face of the wearer around the nose in air tight relation; and
   at least one opening formed in said inner plenum to permit gas to flow into said outer plenum, wherein said secondary seal includes a seal adapted for inflation by the gas flowing into said outer plenum.

10. A respirator mask for delivering a gas to a wearer comprising:
    an inner plenum with a gas inlet and a manifold adapted to fit under the nose of the wearer;
    a pair of nasal inserts projecting from said manifold for insertion into the nostrils of the wearer to deliver the gas, said nasal inserts defining primary seals adapted to contact the nasal passages in air tight relation;
    an outer plenum extending from said inner plenum to an outer edge adapted to surround at least the nose of the wearer;
    a secondary seal mounted on said outer edge of said outer plenum and adapted to contact the face of the wearer around the nose in air tight relation, wherein said secondary seal includes a seal adapted for inflation by the gas flowing into said outer plenum; and
    at least one opening formed in said inner plenum to permit gas to flow into said outer plenum;
    wherein a vent aperture is formed in said inner plenum outside said outer plenum to expel gases exhaled by the wearer.

11. A method of treating a respiratory ailment comprising connecting a source of pressurized gas to an inner plenum of a respirator mask having an outer plenum configured to cover only the nose of a patient, the inner plenum extending into the outer plenum and mounting a pair of nasal inserts, the portion of the inner plenum within the outer plenum further having at least one opening formed therein;
    mounting the respirator mask to the face of a patient over the patient's nose such that the nasal inserts form substantially air-tight primary seals with the patient's nose and the outer plenum forms a substantially airtight secondary seal around the patient's nose;

activating the source of pressurized gas to supply positive gas pressure to the mask, wherein a portion of the pressurized gas flows from the inner plenum to the outer plenum via the opening to create a region of intermediate gas pressure between the primary and secondary seals.

12. A method of treating a respiratory ailment comprising connecting a source of pressurized gas to an inner plenum of a respirator mask having an outer plenum configured to cover only the nose of a patient, the inner plenum extending into the outer plenum and mounting a pair of nasal inserts, the portion of the inner plenum within the outer plenum further having at least one opening formed therein;

mounting the respirator mask to the face of a patient over the patient's nose such that the nasal inserts form substantially air-tight primary seals with the patient's nose and the outer plenum forms a substantially airtight secondary seal around the patient's nose;

activating the source of pressurized gas to supply positive gas pressure to the mask, wherein a portion of the pressurized gas flows from the inner plenum to the outer plenum via the opening to create a region of intermediate gas pressure between the primary and secondary seals; and using the gas pressure in the outer plenum to inflate a seal carried by the outer plenum.

13. A respirator mask for delivering a gas to a wearer comprising:

an inner plenum with a gas inlet and a manifold adapted to fit under the nose of the wearer;

a pair of nasal inserts projecting from said manifold for insertion into the nostrils of the wearer to deliver the gas, said nasal inserts defining primary seals adapted to contact the nasal passages in air tight relation;

an outer plenum extending from said inner plenum to an outer edge adapted to surround at least the nose of the wearer;

a secondary seal mounted on said outer edge of said outer plenum and adapted to contact the face of the wearer around the nose in air tight relation; and at least one opening formed in said inner plenum so as to permit gas to flow into said outer plenum without passing through said nasal inserts.

14. A method of treating a respiratory ailment comprising connecting a source of pressurized gas to an inner plenum of a respirator mask having an outer plenum configured to cover only the nose of a patient, the inner plenum extending into the outer plenum and mounting a pair of nasal inserts, the portion of the inner plenum within the outer plenum further having at least one opening formed therein;

mounting the respirator mask to the face of a patient over the patient's nose such that the nasal inserts form substantially air-tight primary seals with the patient's nose and the outer plenum forms a substantially airtight secondary seal around the patient's nose;

activating the source of pressurized gas to supply positive gas pressure to the mask, wherein a first portion of the pressurized gas flows from the inner plenum into the nasal inserts and a second portion of the pressurized gas flows from the inner plenum to the outer plenum via the opening to create a region of intermediate gas pressure between the primary and secondary seals.

* * * * *